(12) United States Patent
Biggadike et al.

(10) Patent No.: US 7,291,608 B2
(45) Date of Patent: Nov. 6, 2007

(54) ANTI-INFLAMMATORY 17.β.-CARBOTHIOATE ESTER DERIVATIVES OF ANDROSTANE WITH A CYCLIC ESTER GROUP IN POSITION 17.α

(75) Inventors: Keith Biggadike, Stevenage (GB); Paul Jones, Stevenage (GB); Jeremy John Payne, Stevenage (GB)

(73) Assignee: Glaxo Group Limited, Greenford, OK (US)

( * ) Notice: Subject to any disclaimer, the term of this patent is extended or adjusted under 35 U.S.C. 154(b) by 698 days.

(21) Appl. No.: 10/478,893

(22) PCT Filed: Apr. 30, 2002

(86) PCT No.: PCT/GB02/01971

§ 371 (c)(1), (2), (4) Date: Nov. 24, 2003

(87) PCT Pub. No.: WO02/088167

PCT Pub. Date: Nov. 7, 2002

(65) Prior Publication Data

US 2004/0171597 A1 Sep. 2, 2004

(30) Foreign Application Priority Data

Apr. 30, 2001 (GB) ................. 0110578.2
Nov. 22, 2001 (GB) ................. 0127988.4
Feb. 2, 2002 (GB) ................. 0202442.0
Feb. 5, 2002 (GB) ................. 0202637.5

(51) Int. Cl.
A61K 31/56 (2006.01)
C07J 3/00 (2006.01)

(52) U.S. Cl. .................. 514/179; 514/171; 514/180; 552/610

(58) Field of Classification Search ............. 552/610; 514/171, 179, 180
See application file for complete search history.

(56) References Cited

U.S. PATENT DOCUMENTS

| | | | |
|---|---|---|---|
| 3,067,197 A | 12/1962 | Agnello et al. |
| 3,312,590 A | 4/1967 | Elks et al. |
| 3,506,694 A | 4/1970 | Oxley |
| 3,557,162 A | 1/1971 | Voorschoten et al. |
| 3,639,434 A | 2/1972 | Oxley et al. |
| 3,755,302 A | 8/1973 | Ercoli et al. |
| 3,828,080 A | 8/1974 | May et al. |
| 3,856,828 A | 12/1974 | Phillipps et al. |
| 3,891,631 A | 6/1975 | Phillips et al. |
| 3,981,894 A | 9/1976 | Phillipps et al. |
| 3,989,686 A | 11/1976 | Phillipps et al. |
| 4,093,721 A | 6/1978 | Phillipps et al. |
| 4,113,680 A | 9/1978 | Kamano et al. |
| 4,187,301 A | 2/1980 | Edwards |
| 4,188,385 A | 2/1980 | Edwards |
| 4,198,403 A | 4/1980 | Alvarez |
| 4,221,787 A | 9/1980 | Bodor et al. |
| 4,261,984 A | 4/1981 | Alvarez |
| 4,263,289 A | 4/1981 | Edwards |
| 4,267,173 A | 5/1981 | Draper |
| 4,285,937 A | 8/1981 | Kalvoda |
| 4,310,466 A | 1/1982 | Edwards |
| 4,335,121 A | 6/1982 | Phillips et al. |
| 4,377,575 A | 3/1983 | Stache et al. |
| 4,472,393 A | 9/1984 | Shapiro |
| 4,607,028 A | 8/1986 | Schmidlin |
| 4,710,495 A | 12/1987 | Bodor |
| 4,861,765 A | 8/1989 | Mitsukuchi et al. |
| 4,992,474 A | 2/1991 | Skidmore et al. |
| 4,994,439 A | 2/1991 | Longenecker et al. |
| 4,996,335 A | 2/1991 | Bodor |
| 5,063,222 A | 11/1991 | Komoto et al. |
| 5,081,113 A | 1/1992 | Claussner et al. |
| 5,202,316 A | 4/1993 | Claussner et al. |
| 5,250,293 A | 10/1993 | Gleich |
| 5,362,721 A | 11/1994 | Stache et al. |
| 5,420,120 A | 5/1995 | Boltralik |
| 5,658,549 A | 8/1997 | Akehurst et al. |
| 5,707,984 A | 1/1998 | Tjoeng et al. |

(Continued)

FOREIGN PATENT DOCUMENTS

BE 889563 11/1981

(Continued)

OTHER PUBLICATIONS

Kooreman et al., "The synthesis of 17-esters of corticosteroids protection of 11β-hydroxyl by the trimethylsilyl group," *Synthetic Communications* 1(2):81-87 (1971).

(Continued)

*Primary Examiner*—Barbara P. Badio
(74) *Attorney, Agent, or Firm*—James P. Riek

(57) ABSTRACT

There are provided compounds of formula (I)

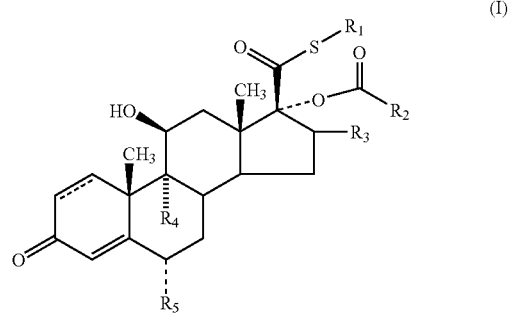

wherein the variables are as defined by the present specification; and solvates thereof, processes for preparing them and their use in therapy.

45 Claims, No Drawings

U.S. PATENT DOCUMENTS

| | | | |
|---|---|---|---|
| 5,837,699 A | 11/1998 | Sequeira et al. |
| 5,849,265 A | 12/1998 | Li-Bovet et al. |
| 5,889,015 A | 3/1999 | Sequeira et al. |
| 5,919,776 A | 7/1999 | Hagmann et al. |
| 5,972,920 A | 10/1999 | Seidel |
| 5,981,517 A | 11/1999 | Bodor |
| 6,057,307 A | 5/2000 | Sequeira et al. |
| 6,127,353 A | 10/2000 | Yuen et al. |
| 6,136,294 A | 10/2000 | Adjei et al. |
| 6,197,761 B1 | 3/2001 | Biggadike et al. |
| 6,261,539 B1 | 7/2001 | Adjei et al. |
| 6,395,300 B1 | 5/2002 | Straub et al. |
| 6,537,983 B1 | 3/2003 | Biggadike et al. |
| 6,750,210 B2 | 6/2004 | Biggadike |
| 6,759,398 B2 | 7/2004 | Biggadike |
| 6,777,399 B2 | 8/2004 | Biggadike et al. |
| 6,777,400 B2 | 8/2004 | Biggadike et al. |
| 6,787,532 B2 | 9/2004 | Biggadike et al. |
| 6,858,593 B2 | 2/2005 | Biggadike et al. |
| 6,858,596 B2 | 2/2005 | Biggadike et al. |
| 6,878,698 B2 | 4/2005 | Biggadike et al. |
| 6,921,757 B2 | 7/2005 | Cuenoud et al. |
| 7,101,866 B2 | 9/2006 | Biggadike et al. |
| 7,125,985 B2 | 10/2006 | Biggadike et al. |
| 7,132,532 B2 | 11/2006 | Biggadike et al. |
| 7,144,845 B2 | 12/2006 | Biggadike et al. |
| 2002/0081266 A1 | 6/2002 | Woolfe et al. |
| 2002/0103392 A1 | 8/2002 | Stache et al. |
| 2002/0165211 A1 | 11/2002 | Biggadike et al. |
| 2002/0173496 A1 | 11/2002 | Biggadike |
| 2002/0177581 A1 | 11/2002 | Biggadike |
| 2003/0073676 A1 | 4/2003 | Biggadike et al. |
| 2003/0109511 A1 | 6/2003 | Biggadike et al. |
| 2003/0144257 A1 | 7/2003 | Biggadike et al. |
| 2003/0158163 A1 | 8/2003 | Cuenoud et al. |
| 2004/0053904 A1 | 3/2004 | Komoto et al. |
| 2005/0163724 A1 | 7/2005 | Miyadai et al. |

FOREIGN PATENT DOCUMENTS

| | | |
|---|---|---|
| DE | 1059906 | 6/1959 |
| DE | 2031205 | 2/1971 |
| DE | 2336693 | 2/1975 |
| DE | 2538569 | 3/1977 |
| DE | 10237739 | 2/2004 |
| EP | 0004773 | 10/1979 |
| EP | 0057401 | 8/1982 |
| EP | 0135476 | 3/1985 |
| EP | 0179583 | 4/1986 |
| EP | 0389368 | 9/1990 |
| EP | 0389369 | 9/1990 |
| EP | 0393658 | 10/1990 |
| EP | 0416951 | 3/1991 |
| EP | 0418716 | 3/1991 |
| EP | 0470617 | 2/1992 |
| EP | 0521455 | 1/1993 |
| EP | 0640616 | 3/1995 |
| EP | 0646593 | 4/1995 |
| FR | 580494 | 10/1986 |
| GB | 1296458 | 11/1972 |
| GB | 1384372 | 2/1975 |
| GB | 1438940 | 6/1976 |
| GB | 1517278 | 7/1978 |
| GB | 2079755 | 1/1982 |
| GB | 2140800 | 12/1984 |
| IL | 109656 | 2/1998 |
| JP | 04208267 | 7/1992 |
| JP | 8291072 | 11/1996 |
| JP | 8291073 | 11/1996 |
| WO | WO 89/03390 | 4/1989 |
| WO | 92/14472 | 9/1992 |
| WO | 94/21229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | WO 97/21721 | 6/1997 |
| WO | WO 97/21724 | 6/1997 |
| WO | 97/24365 | 7/1997 |
| WO | WO 97/40836 | 11/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | WO 99/32089 | 7/1999 |
| WO | 00/16814 | 3/2000 |
| WO | 00/33892 | 6/2000 |
| WO | 00/38811 | 7/2000 |
| WO | 00/57401 | 8/2000 |
| WO | WO 00/49993 | 8/2000 |
| WO | WO 00/66522 | 11/2000 |
| WO | 01/012001 | 1/2001 |
| WO | 02/00199 | 1/2001 |
| WO | 01/15744 | 3/2001 |
| WO | 01/20331 | 3/2001 |
| WO | 01/54664 | 8/2001 |
| WO | 01/62722 | 8/2001 |
| WO | WO 01/54481 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/007767 | 1/2002 |
| WO | 0200679 | 1/2002 |
| WO | WO 02/000679 | 1/2002 |
| WO | 02/013868 | 2/2002 |
| WO | WO 02/012265 | 2/2002 |
| WO | WO 02/012266 | 2/2002 |
| WO | 02/026723 | 4/2002 |
| WO | WO 02/36106 | 5/2002 |
| WO | WO 02/47667 | 6/2002 |
| WO | 02/053186 | 7/2002 |
| WO | WO 02/051422 | 7/2002 |
| WO | 02/066422 | 8/2002 |
| WO | 02/070490 | 9/2002 |
| WO | 02/076933 | 10/2002 |
| WO | 02/085296 | 10/2002 |
| WO | 02/088167 | 11/2002 |
| WO | WO 02/100879 | 12/2002 |
| WO | 02/008243 | 1/2003 |
| WO | WO 03/000241 | 1/2003 |
| WO | 03/013427 | 2/2003 |
| WO | 03/033000 | 4/2003 |
| WO | 03/040691 | 5/2003 |
| WO | WO 03/035668 | 5/2003 |
| WO | WO 03/042229 | 5/2003 |
| WO | WO 03/042230 | 5/2003 |
| WO | WO 03/048181 | 6/2003 |
| WO | WO 03/062259 | 7/2003 |
| WO | WO 03/064445 | 8/2003 |
| WO | WO 03/066656 | 8/2003 |
| WO | WO 03/072592 | 9/2003 |
| WO | WO 03/086399 | 10/2003 |
| WO | WO 03/105859 | 12/2003 |
| WO | WO 04/013156 | 2/2004 |
| ZA | 872389 | 4/1987 |

OTHER PUBLICATIONS

Shapiro et al., "17-esters and 17,21-diesters of 9α,11β-dichlorocorticoids. Synthesis and anti-inflammatory activity," *Steroids* 9(2):143-156 (1967).

Togashi et al., "9-fluoro-11β, 17, 21-trihydroxy-16α-methyl-1,4-pregnadiene-3, 20-dione 21-cyclohexanecarboxylate 17-cyclopropanecarboxylate (ST126)," Oyo Yakuri 63(5/6):61-77 (2002).

Phillipps, et. al., "Synthesis and Structure-Activity Relationships in a Series of Antiinflammatory Corticosteroid Analogues, Halomethyl Androstane-17Beta-Carbothiates and-17Beta-Carboselenoates", Journal of Medicinal Chemistry, vol. 37, No. 22, Oct. 1, 1994, pp. 3722.

Isogai, et. al., "Binding Affinities Of Mometasone Furoate and Related Compounds Including its Metabolites for the Glucocorticoid Receptor of Rat Skin Tissue", Journal of Steroid Biochemistry and Molecular Biology, vol. 44, No. 2, 1993, pp. 141-145.

Ueno, et al, "Synthesis and Evaluation of Antiinflammatory Activities of a Series of Corticosteroid 17. Alpha -Esters Containing a Functional Group", Journal of Medicinal Chemistry, vol. 34, No. 8, Aug. 1, 1991, pp. 2468-2473.

Janette M. Mahoney et al., "Drug effects on the neovascularization response to silver nitrate cauterization of the rat cornea" Current Eye Research, vol. 4, No. 5, 1985, pp. 531-535.

Richard A. Kenley et al., "An Automated, Column-Switching HPLC Method for Analyzing Active and Exipient Materials in Both Cream and Ointment Formulations," Drug Development and Industrial Pharmacy, vol. 11 (9&10), 1985, pp. 1781-1796.

R. Woodford et al., "Activity and bioavailability of a new steroid (Timobesone acetate) in cream and ointment compared with Lidex and Dermovate creams and ointments and Betnovate cream" Int'l Journal of Pharmaceuticals, vol. 26 (1985) pp. 145-155.

Denis J. Kertesz et al., "Thiol Esters from Steroid 17β-Carboxylic Acids: Carboxylate Activation and Internal Participation by 17 α-Acylates" J. Org. Chem., vol. 51, 1986, pp. 2315-2328.

Popper, T.L., et al., "Structure-Activity Relationship of a series of novel topical corticosteroids", Journal of Steroid Biochemistry 1987, vol. 27, 840-841.

Shapiro, E.L., et al., Al., "17 Heteroaoyl Esters of Corticosteriods 2. 11 Beta Hydroxy Series." Journal of medicinal Chemistry, American Chemical Society, Washington, US, vol. 30. No. 9, 1987, pp. 1581-1588.

John T. H. Ong et al., "Micellar Solubilization of Timobesone Acetate in Aqueous and Aqueous Propylene Glycol Solutions of Nonionic Surfactanta", Pharmaceutical Research, vol. 5, No. 11, 1988, pp. 704-708.

John T. H. Ong et al., Intrinsic Potencies of Novel Thiol Ester Corticosteroids RS-85095 and RS-21314 as Compared With Clobetasol 17-Propionate and Fluocinonide Arch Dermatol, vol. 125, Dec. 1989, pp. 1662-1665.

S.J. Lane et al., "Evaluation of a New Capillary Electrochromatography/Mass Spectromrtry Interface Using Short Columns and High Field Strengths for Rapid and Efficient Analyses," Rapid Communications in Mass Spectrometry, vol. 10, 1996, pp. 733-736.

Franklin I. Aigbirhio et al., "Automated Radiosynthesis of No-carrier-added [S-fluoromethyl-$^{18}$F]Fluticasone Propionate as a Radiotracer for Lung Deposition Studies with PET" Journal of Labelled Compounds and Radiopharmaceuticals, vol. 39, No. 7, 1997, pp. 569-584.

Nisha Mistry et al., "Characterisation of impurities in bulk drug batches of fluticasone propionate using directly coupled HPLC-NMR spectroscopy and HPLC-MS," Journal of Pharmaceutical and Biomedical Analysis vol. 16, 1997, pp. 697-705.

Knobil, K., et al., Al., "Adding Salmetrol Is More Effective Than Increasing The Dose Of Fluticasone For Patients With Asthma Who Are Symptomatic On Low Dose Fluticasone," European Respiratory review, Copenhagen, DK, vol. 12, No. SUPPL Dec. 29, 1998 (1998-12), pp. 19S-20S.

Nisha Mistry et al., Impurity profiling in bulk pharmaceutical batches using 19F NMR spectroscopy amd distinction between monomeric and dimeric impurities by NMR-based diffusion measurements, Journal of Pharmaceutical and Biomedical Analysis, vol. 19, 1999, pp. 511-517.

N. Smith et al., "Comparison of the electroosmotic flow profiles and selectivity of stationaty phases used in capillary electrochromatography," Journal of Chromatography A., vol. 832, 1999, pp. 44-54.

R.C. Garner et al., "A validation study comparing accelerator MS and liquid scintillation counting for analysis of $^{14}$C-labelled drugs in plasma, urine and faecal extracts", Journal of Pharmaceutical and Biomedical Analysis vol. 24, 2000, pp. 197-209.

Harold S. Nelson et al., "Fluticasone propionate/salmeterol combination provides more effective asthma control than low-dose inhaled corticosteroid plus montelukast," J. Allergy Clin. Immunol., vol. 106, No. 6, Dec. 2000, pp. 1088-1095.

Gunnar Johansson et al., "comparison of Salmetrol/Fluticasone Propionate Combination With Budesonide in Patients With Mild-to-Moderate Asthma" Clin. Drug Invest. vol. 21, No. 9, 2001, pp. 633-642.

Bertil Pettersson et al., Re-evaluation of the classical *Mycoplasma lipophilum* cluster (Weisburg et al. 1989) and description of two new clusters in the hominis group based on 16S rDNA sequences, int'l Journal of Systematic & Evolutionary Microbiology (2001) vol. 51, pp. 633-643.

Sarah A. Lewis et al., "Association of specific allergen senitzation with socioeconomic factors and allergic disease in a population of Boston women", J. Allergy Clin. Immunol., vol. 107, No. 4, Apr. 2001, pp. 615-622.

Katherine A. Lyseng-Williamson et al., "Inhaled Slmeterol/Fluticasone Propionate Combination in Chronic Obstructive Pulmonary Disease," Am. J. Respir. Med. vol. 1, No. 4, 2002, pp. 273-282.

Jeffrey W. Millard et al., "Solubilization by consolvents Establishing useful constants for the log-linear model," Int'l Journal of Pharmaceutics vol. 245, 2002, pp. 153-166.

C. Baumgarten et al., "Initial Treatment of Symptomatic Mild to moderate Bronchial Asthma with the Salmeterol/Fluticasone Propionate (50/250µg) Combination Product (SAS 40023)" European Journal of Medical Research 2002, vol. 7, pp. 1-7.

Stephen J. Fpwler et al., "Step-down therapy with low-dose fluticasone-salmeterol combination or medium-dose hydrofluoroalkane 134a-beclomethasone alone" J. Allergy Clin. Immunol., vol. 109, No. 6, Jun. 2002, pp. 929-935.

Elizabeth F. Juniper et al., "Impact of Inhaled Salmeterol/Fluticasone Propionate Combination Product versus Budersonide on the Health-Related Quality of Life of Patient with Asthma," Am. J. Respir. Med., vol. 1, No. 6, 2002, pp. 435-440.

William Busse et al., "Steroid-sparing effects of fluticasone propionate 100 µg and salmeterol 50 µg administered twice daily in a single product in patients previously controlled with fluticaasone propionate 250 µg administered twice daily" J. Allergy Clin. Immunol., vol. 111, No. 1, Jan. 2003, pp. 57-65.

Peter J Barnes, "Novel approaches and targets for treatment of chronic obstructive Pulmonary Disease" American Journal of Respiratory and Critical Care Medicine, vol. 160, 1999, pp. S72-S79.

B.J. O Conner: "Combination Therapy", Pulmonary Pharmacology and Therapeutics, vol. 11, No. 5/6, 1998, pp. 397 - 399.

Peter J Barnes, "Chronic Obstructive Pulmonary Disease: new opportunities for drug development" Trends in Pharmacological Sciences, Elsevenir Trends Journal, vol. 19, No. 10, 1998, pp. 415 - 423.

Simon Bowler, "Long acting beta agonists", Austrailian Family Physician, vol. 27, No. 12, 1998, pp. 1114-1118.

Naedle-Risha R et al, "Dual components of optimal asthma therapy: Scientific and clinical rationale for the use of long acting beta-agonists with inhales corticosteroids", The Journal of the American Osteopathic Association, vol. 101, No. 9, Sep. 2001, pp. 2001-09.

T Van Der Molen et al, "Effects of the long Acting Beta Agonist Formoterol on Asthma Control in Asthmatic Patients Using Inhaled Corticosteroids", vol. 52, No. 6, 1997, pp. 535-539.

B.N. Lutsky et al, "A Novel Class of potent Topical Anti-inflammatory Agents: 17 Benzoylated, 7 - Halogeno Substituted Corticosteroids", Arzeneimittel Forschung, vol. 29, No. 11, Nov. 1979, pp. 1662-1667.

Peter J. Barnes, "Efficacy of Inhaled Corticosteroids in Asthma", The Journal of Allergy and Clinical Immunology, vol. 102, No. 4, pp. 531-538.

CAS Registry No. 102113-40-6.

Li et al., "Synthesis of aryl 5-(2-chlorophenyl)-2-furoates under phase transfer catalysis," *Synthetic Communications* 32(20):3081-3086 (2002).

Moreno-Vargas et al., "Synthesis and glycosidase inhibitory activities of 5-(1',4'-dideoxy-1',4'-imino-D-erythrosyl)-2-methyl-3-furoic acid (=5-[(3S,4R)-3,4-dihydroxypyrrolidin-2-yl]-2methylfuran-3-carboxylic acid) derivatives: New leads as selective α-L-fucosidase and β-galactosidase inhibitors," *Helvetica Chimica Acta* 86:1894-1913 (2003).

Tanaka et al., "Synthesis of 4H-furo[3,2-b]indole derivatives. III (1). Preparation of 4H-furo[3,2-b]indole-2-carboxylic acid derivatives," *Journal Heterocyclic Chemisrty* 16:785-788 (1979).

Wenkert et al., "Short syntheses of furan and catechol derivatives. A synthesis of hydrourushiol[1,2]," *Journal American Chemical Society* 105:2021-2029 (1983).

Shapiro et al., "Synthesis and structure-activity studies of corticosteroid 17-heterocyclic aromatic esters. 1. 9α, 11β dichloro series," *Journal of medicinal chemistry* 30(6):1068-1073 (1987).

U.S. Appl. No. 10066964 filed on Feb. 4, 2002.
U.S. Appl. No. 10/067,010 filed on Feb. 4, 2002.
U.S. Appl. No. 10/066,836 filed on Feb. 4, 2002.
U.S. Appl. No. 10/200,364 filed on Jul. 2002.
U.S. Appl. No. 10/281,735 filed on Oct. 28, 2002.
U.S. Appl. No. 10/241,658 filed on Sep. 11, 2002.
U.S. Appl. No. 10/066,951 filed on Feb. 4, 2002.
U.S. Appl. No. 10/067,020 filed on Feb. 4, 2002.

Sakagami et al., "Mucoadhexive BDP microspheres for powder inhalation-their unique pahracokinetic-pharmacodynamic profiles," *Respiratory Drug Delivery VI*, pp. 193-199 (1998).

PCT/GB01/03495 Written Opinion, date of mailing Apr. 4, 2002.
PCT/GB01/03495 International Preliminary Examination Report, date of Mailing Aug. 30, 2002.

U.S. Appl. No. 10/343,842 filed Aug. 3, 2001.
U.S. Appl. No. 10/918,770 filed Aug. 13, 2004.
U.S. Appl. No. 10/480,071 filed Jun. 15, 2004.
U.S. Appl. No. 10/492,813 filed Sep. 20, 2004.
U.S. Appl. No. 10/503,540, filed Mar. 25, 2005.
U.S. Appl. No. 10/862,692, filed Jun. 7, 2004.
U.S. Appl. No. 10/862,793, filed Jun. 7, 2004.
U.S. Appl. No. 11/428,853, filed Jul. 6, 2006.
U.S. Appl. No. 10/503,394, filed Jan. 18, 2005.
U.S. Appl. No. 10/503,396, filed Jan. 6, 2005.
U.S. Appl. No. 10/918,779, filed Aug. 13, 2004.
U.S. Appl. No. 10/502,902, filed Jan. 28, 2005.
U.S. Appl. No. 10/503,417, filed Aug. 3, 2004.
U.S. Appl. No. 10/503,000, filed Apr. 14, 2005.
U.S. Appl. No. 10/863,878, filed Jun. 8, 2004.
U.S. Appl. No. 10/503,114, filed Oct. 20, 2004.
U.S. Appl. No. 10/503,396, filed Jan. 6, 2005.
U.S. Appl. No. 10/853,500, filed May 25, 2004.
U.S. Appl. No. 10/502,966, filed Apr. 14, 2005.

Phillipps, G.H. et al. "Synthesis and structure activity Relationships in a series of Anti-inflammatory Corticosteroid Analogues, Halomethyl Androstane- 17β-carbothioates and -17β-carboselenoates." Journal of Medicinal Chemistry 1994, 37, 3717-3729.

ANTI-INFLAMMATORY 17.β.-CARBOTHIOATE ESTER DERIVATIVES OF ANDROSTANE WITH A CYCLIC ESTER GROUP IN POSITION 17.α

This application is filed pursuant to 35 USC 371 as a United States National Phase Application of International Patent Application Serial No. PCT/GB02/01971 filed 30 Apr. 2002, which claims priority from: GB 0110578.2 filed on 30 Apr. 2001; GB 0127988.4 filed on 22 Nov. 2001; GB 0202442.0 filed 2 Feb. 2002; and GB 0202637.5 filed on 5 Feb. 2002, all of which were filed in the United Kingdom.

The present invention relates to novel anti-inflammatory and anti-allergic compounds of the androstane series and to processes for their preparation. The present invention also relates to pharmaceutical formulations containing the compounds and to therapeutic uses thereof, particularly for the treatment of inflammatory and allergic conditions.

Glucocorticoids which have anti-inflammatory properties are known and are widely used for the treatment of inflammatory disorders or diseases such as asthma and rhinitis. For example, U.S. Pat. No. 4,335,121 discloses 6α,9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced it remains an object of research to produce new molecules which have excellent anti-inflammatory properties, with predictable pharmacokinetic and pharmacodynamic properties, with an attractive side effect profile, and with a convenient treatment regime.

Certain novel androstane derivatives are disclosed in WO02/12265 and WO02/12266 (Glaxo Group), both of these documents being published after the earliest priority date of this patent application.

We have identified a novel series of glucocorticoids, which substantially meets these objectives.

Thus, according to one aspect of the invention, there is provided a compound of formula (I)

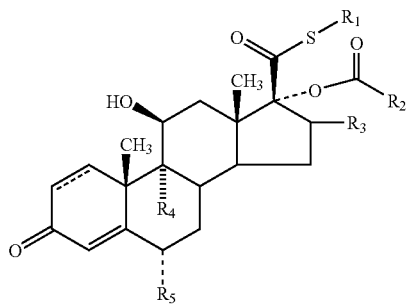

wherein
$R_1$ represents $C_{1-6}$ alkyl or $C_{1-6}$ haloalkyl;
$R_2$ represents $C_{3-8}$ cycloalkyl or $C_{3-8}$ cycloalkenyl either of which may optionally be substituted by one or more groups selected from oxo, methyl, methylene and halogen;
$R_3$ represents hydrogen, methyl (which may be in either the α or β configuration) or methylene;
$R_4$ and $R_5$ are the same or different and each represents hydrogen or halogen; and === represents a single or a double bond;

and solvates thereof.

Examples of solvates include hydrates.

References hereinafter to a compound according to the invention includes both compounds of formula (I) and solvates thereof.

It will be appreciated that the invention includes within its scope all stereoisomers (including enantiomers and diastereoisomers) of the compounds of formula (I) and mixtures thereof.

Preferably, the absolute stereochemistry will be as shown in the representation of compounds of formula (I).

Examples of $C_{1-6}$ haloalkyl that $R_1$ may represent include $C_{1-6}$ alkyl substituted by 1–3 halogen atoms, preferably 1 halogen atom. Preferred halogen atoms are selected from bromine, chlorine and fluorine.

Examples of $C_{3-6}$ cycloalkyl groups that $R_2$ may represent include cyclopropyl, cyclobutyl, cyclopentyl and cyclohexyl and substituted derivatives such as methylcyclopropyl (eg 1-methylcyclopropyl or 2-methylcyclopropyl), dichlorocyclopropyl (eg 2,2-dichloropropyl), methyldichlorocyclopropyl (eg 1-methyl-2,2-dichlorocyclopropyl), exomethylenecyclobutyl (eg 3-exomethylenecyclobutyl), tetramethylcyclopropyl (eg 2,2,3,3-tetramethylcyclopropyl) and methycyclobutyl (eg 1-methylcyclobutyl). Other examples include dimethylcyclobutyl (eg 3,3-dimethylcyclobutyl), difluorocyclobutyl (eg 3,3-difluorocyclobutyl), methylcyclopentyl (eg 1-methylcyclopentyl). A further example includes oxocyclobutyl (eg 3-oxocyclobutyl).

Examples of $C_{3-4}$ cycloalkenyl groups that $R_2$ may represent include alkenyl groups containing 1 or more double bonds (not being aromatic groups) such as cyclohexenyl eg cyclohex-2,3-enyl.

We prefer $R_1$ to represent fluoromethyl, chloromethyl, bromomethyl or 2'-fluoroethyl, especially fluoromethyl.

Preferably, $R_2$ represents $C_{3-8}$ cycloalkyl or $C_{3-8}$ cycloalkenyl either of which may optionally be substituted by one or more groups selected from methyl, methylene and halogen. In an alternative aspect, $R_2$ represents $C_{3-8}$ cycloalkyl or $C_{3-8}$ cycloalkenyl either of which may be substituted by oxo eg 3-oxocyclobutyl.

We prefer $R_2$ to represent $C_{3-8}$ cycloalkyl optionally substituted by one or more methyl and/or halogen groups. We particularly prefer $R_2$ to represent $C_{3-6}$ cycloalkyl, more preferably $C_{3-4}$ cycloalkyl, optionally substituted by one or more methyl or chlorine groups.

We also prefer $R_2$ to represent $C_{3-6}$ cycloalkyl substituted by methylene.

In one set of preferred compounds, $R_2$ is unsubstituted or substituted by at most one methyl or chlorine group. More preferably, $R_2$ is substituted by one methyl group, especially in the 1-position, eg 1-methyl cyclopropyl or 1-methylcyclobutyl.

In another set of preferred compounds, $R_2$ is substituted by more than one methyl group, eg 2,2,3,3-tetramethylcyclopropyl.

We prefer R₃ to represent methyl, especially methyl in the α configuration.

Compounds of formula (I) in which $R_4$ and $R_5$, which can be the same or different, each represents hydrogen, fluorine or chlorine, particularly hydrogen or fluorine, are preferred. Especially preferred are compounds in which both $R_4$ and $R_5$ are fluorine.

Preferably, ═ represents a double bond.

It is to be understood that the present invention covers all combinations of particularly and preferred groups referred to hereinabove.

Preferred compounds of formula (I) include:
17α-(Cyclobutylcarbonyl)oxy-6α,9α-difluoro-11β-hydroxy-16α-methyl-3-oxo-androsta-1,4-diene-17β-carbothioic acid S-fluoromethyl ester;
17α-(Cyclopentylcarbonyl)oxy-6α,9α-difluoro-11β-hydroxy-16α-methyl-3-oxo-androsta-1,4-diene-17β-carbothioic acid S-fluoromethyl ester;
17α-(Cyclohexylcarbonyl)oxy-6α,9α-difluoro-11β-hydroxy-16α-methyl-3-oxo-androsta-1,4-diene-17β-carbothioic acid S-fluoromethyl ester;
17α-(Cyclopropylcarbonyl)oxy-6α,9α-difluoro-11β-hydroxy-16α-methyl-3-oxo-androsta-1,4-diene-17β-carbothioic acid S-fluoromethyl ester;
6α,9α-Difluoro-11β-hydroxy-16α-methyl-17α-(3-methycyclopropylcarbonyl)oxy-3-oxo-androsta-1,4-diene-17β-carbothioic acid S-fluoromethyl ester;
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-fluoromethyl ester;
17α-(2,2-Dichloro-1-methycyclopropylcarbonyl)oxy-6α,9α-difluoro-11β-hydroxy-16α-methyl-3-oxo-androsta-1,4-diene-17β-carbothioic acid S-fluoromethyl ester;
17α-(2,2-Dichlorocyclopropylcarbonyl)oxy-6α,9α-difluoro-11β-hydroxy-16α-methyl-3-oxo-androsta-1,4-diene-17β-carbothioic acid S-fluoromethyl ester;
6α,9α-Difluoro-11β-hydroxy-16α-methyl-17α-(3-methylenecyclobutylcarbonyl)oxy-3-oxo-androsta-1,4-diene-17β-carbothioic acid S-fluoromethyl ester;
6α,9-Difluoro-11β-hydroxy-16α-methyl-17α-(2-methylcyclopropylcarbonyl)oxy-3-oxo-androsta-1,4-diene-17β-carbothioic acid S-fluoromethyl ester;
6α,9α-Difluoro-11β-hydroxy-16α-methyl-17α-(1-methylcyclobutylcarbonyl)oxy-3-oxo-androsta-1,4-diene-17β-carbothioic acid S-fluoromethyl ester;
6α,9α-Difluoro-17α-(3,3-dimethylcyclobutylcarbonyl)oxy-11β-hydroxy-16α-methyl-3-oxo-androsta-1,4-diene-17β-carbothioic acid S-fluoromethyl ester;
6α,9α-Difluoro-17α-(3,3-difluorocyclobutylcarbonyl)oxy-11β-hydroxy-16α-methyl-3-oxo-androsta-1,4-diene-17β-carbothioic acid S-fluoromethyl ester;
6α,9α-Difluoro-11β-hydroxy-16α-methyl-17α-(1-methylcyclopentylcarbonyl)oxy-3-oxo-androsta-1,4-diene-17β-carbothioic acid S-fluoromethyl ester;
6α,9α-Difluoro-11β-hydroxy-16α-methyl-3-oxo-17α-(3-oxocyclobutylcarbonyl)oxy-androsta-1,4-diene-17β-carbothioic acid S-fluoromethyl ester.

One particularly preferred compound is the following:
6α,9α-Difluoro-11β-hydroxy-16α-methyl-17α-(1-methycyclopropylcarbonyl)oxy-3-oxo-androsta-1,4-diene-17β-carbothioic acid S-fluoromethyl ester.

Another particularly preferred compound is the following:
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-fluoromethyl ester.

Another particularly preferred compound is the following:
6α,9α-Difluoro-11β-hydroxy-16α-methyl-17α-(1-methylcyclobutylcarbonyl)oxy-3-oxo-androsta-1,4-diene-17β-carbothioic acid S-fluoromethyl ester.

The compounds of formula (I) have potentially beneficial anti-inflammatory or anti-allergic effects, particularly upon topical administration, demonstrated by, for example, their ability to bind to the glucocorticoid receptor and to illicit a response via that receptor with long lasting effect. Hence, the compounds of formula (I) are useful in the treatment of inflammatory and/or allergic disorders, especially in once-per-day therapy.

Examples of disease states in which the compounds of the invention have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents, especially in once-per-day therapy.

There is thus provided as a further aspect of the invention a compound of formula (I) or a physiologically acceptable solvate thereof for use in human or veterinary medicine, particularly in the treatment of patients with inflammatory and/or allergic conditions. Pharmaceutical compositions for once-per-day administration are of particular interest.

According to another aspect of the invention, there is provided the use of a compound of formula (I) or physiologically acceptable solvate thereof for the manufacture of a medicament for the treatment of patients with inflammatory and/or allergic conditions, especially for therapy once-per-day.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof, especially administration once-per-day.

The compounds according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Advantageously compositions for topical administration to the lung include dry powder compositions and spray compositions.

Dry powder compositions for topical delivery to the lung may, for example, be presented in capsules and cartridges for use in an inhaler or insufflator of, for example, gelatine. Formulations generally contain a powder mix for inhalation of the compound of the invention and a suitable powder base such as lactose or starch. Use of lactose is preferred. Each capsule or cartridge may generally contain between 20 μg-10 mg of the compound of formula (I) optionally in combination with another active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Pharmaceutical formulations which are non-pressurised and adapted to be administered as a dry powder topically to the lung via the buccal cavity (especially those which are free of excipient or are formulated with a diluent or carrier such as lactose or starch, most especially lactose) are of particular interest.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. One example formulation is excipient free and consists essentially of (eg consists of) compound of formula (I) (preferably in unsolvated form eg as Form 1) (optionally in combination with another therapeutically active ingredient) and a propellant selected from 1,1,1,2-tetrafluoroethane, 1,1,1,2,3,3,3-heptafluoro-n-propane and mixture thereof. Another example formulation comprises particulate compound of formula (I), a propellant selected from 1,1,1,2-tetrafluoroethane, 1,1,1,2,3,3,3-heptafluoro-n-propane and mixture thereof and a suspending agent which is soluble in the propellant eg an oligolactic acid or derivative thereof as described in WO94/21229. The preferred propellant is 1,1,1,2-tetrafluoroethane. As noted elsewhere in this specification, compound of formula (I) does not appear to form a solvate with 1,1,1,2-tetrafluoroethane. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1–10 μm, preferably 2–5 μm. Particles having a size above 20 μm are generally too large when inhaled to reach the small airways. To achieve these particle sizes the particles of compound of formula (I) as produced may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (eg as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04327). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 μm and not less than 15% will have a MMD of less than 15 μm.

Formulations for administration topically to the nose (eg for the treatment of rhinitis) include pressurised aerosol formulations and aqueous formulations administered to the nose by pressurised pump. Formulations which are non-pressurised and adapted to be administered topically to the nasal cavity are of particular interest. The formulation preferably contains water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

Other possible presentations include the following:

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Advantageously, the formulations of the invention may be buffered by the addition of suitable buffering agents.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 µg–2000 µg, preferably about 20 µg–500 µg of a compound of formula (I). Administration may be once daily or several times daily, for example 2, 3, 4 or 8 times, giving for example 1, 2 or 3 doses each time. The overall daily dose with an aerosol will be within the range 100 µg–10 mg preferably, 200 µg–2000 µg. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising a compound of formula (I) or a physiologically acceptable solvate thereof together with another therapeutically active agent, for example, a $\beta_2$-adrenoreceptor agonist, an anti-histamine, an anti-allergic or an anti-cholinergic.

Examples of $\beta_2$-adrenoreceptor agonists include salmeterol (eg as xinafoate), salbutamol (eg as sulphate), formoterol (eg as fumarate), fenoterol or terbutaline (eg as sulphate). Long-acting $\beta_2$-adrenoreceptor agonists are preferred, especially those having a therapeutic effect over a 24 hour period.

Especially preferred long-acting $\beta_2$ adrenoreceptor agonists are compounds of formula (X)

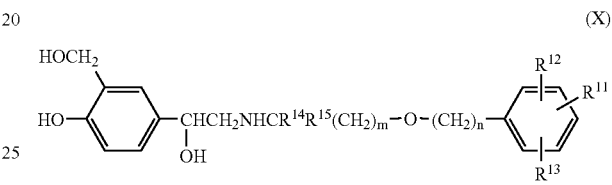

or a salt or solvate thereof, wherein:
m is an integer of from 2 to 8;
n is an integer of from 3 to 11, preferably from 3 to 7;
with the proviso that m+n is 5 to 19, preferably 5 to 12;
$R^{11}$ is —$XSO_2NR^{16}R^{17}$
wherein X is —$(CH_2)_p$— or $C_{2-6}$ alkylene;
$R^{16}$ and $R^{17}$ are independently selected from hydrogen, $C_{1-6}$alkyl, $C_{3-7}$cycloalkyl, $C(O)NR^{18}R^{19}$, phenyl, and phenyl($C_{1-4}$alkyl)-,
or $R^{16}$ and $R^7$, together with the nitrogen to which they are bonded, form a 5-, 6-, or 7-membered nitrogen containing ring, and $R^{16}$ and $R^{17}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{18}$, —$SO_2NR^{18}R^{19}$, —$CONR^{18}R^{19}$, —$NR^{18}C(O)R^{19}$, or a 5-, 6- or 7-membered heterocylic ring;
$R^{18}$ and $R^{19}$ are independently selected from hydrogen, $C_{1-6}$alkyl,
$C_{3-6}$cycloalkyl, phenyl, and phenyl($C_{1-4}$alkyl)-; and
p is an integer of from 0 to 6, preferably from 0 to 4;
$R^{12}$ and $R^{13}$ are independently selected from hydrogen, $C_{1-6}$alkyl, $C_{1-6}$alkoxy, halo, phenyl, and $C_{1-6}$haloalkyl; and
$R^{14}$ and $R^{15}$ are independently selected from hydrogen and $C_{1-4}$alkyl with the proviso that the total number of carbon atoms in $R^{14}$ and $R^{15}$ is not more than 4.

In the compounds of formula (I) the group $R^{11}$ is preferably attached to the meta-position relative to the —O—$(CH_2)_n$— link.
$R^{11}$ preferably represents —$SO_2NR^{16}R^{17}$ wherein $R^{16}$ and $R^{17}$ are independently selected from hydrogen and $C_{1-6}$alkyl, more preferably $R^{11}$ is —$SO_2NH_2$.
$R^{14}$ and $R^{15}$ are preferably independently selected from hydrogen and methyl, more preferably $R^{14}$ and $R^{15}$ are both hydrogen.
m is suitably 4, 5, or 6, and n is suitably 3, 4, 5 or 6. Preferably m is 5 or 6 and n is 3 or 4, such that m+n is 8, 9 or 10, preferably 9.

More especially preferred compounds of formula (X) are compounds of formula (Xa)

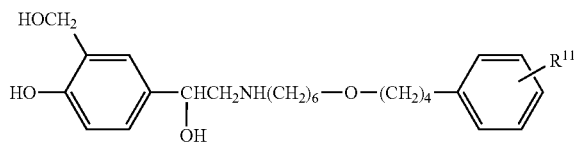

(Xa)

or a salt or solvate thereof, wherein
$R^{11}$ is as defined above for formula (X).

Further more especially preferred compounds of formula (X) are compounds of formula (Xb):

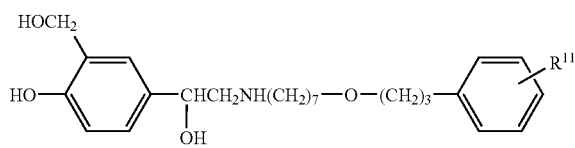

(Xb)

or a salt or solvate thereof, wherein
$R^{11}$ is as defined above for formula (X).

In the compounds of formulae (Xa) and (Xb), the group $R^{11}$ is preferably attached to the meta-position relative to the —O—$(CH_2)_n$—, —O—$(CH_2)_4$— or —O—$(CH_2)_3$— link respectively.

In the compounds of formulae (Xa) and (Xb), $R^{11}$ is preferably —$SO_2NR^{16}R^{17}$ wherein $R^{16}$ and $R^{17}$ are independently selected from hydrogen and $C_{1-6}$alkyl, more preferably $R^{11}$ is —$SO_2NH_2$.

In the definition of $R^{11}$ where '$R^{16}$ and $R^{17}$ together with the nitrogen atom to which they are bonded, form a 5-, 6-, or 7-membered nitrogen containing ring', the term "5-, 6-, or 7-membered nitrogen containing ring" means a 5-, 6-, or 7-membered saturated or unsaturated ring which includes the sulfonamide nitrogen atom and optionally 1 or 2 other heteroatoms independently selected from nitrogen, sulphur, and oxygen. Suitable examples of such a ring include piperidinyl, morpholinyl, and piperazinyl.

In the definition of $R^{11}$, specifically the optional substituents on $R^{16}$ and $R^{17}$, the term "5-, 6-, or 7-membered heterocyclic ring" means a 5-, 6-, or 7-membered fully or partially saturated or unsaturated ring which includes 1, 2, 3 or 4 heteroatoms independently selected from nitrogen, sulphur, and oxygen. Suitable examples of such a ring include pyrrolyl, furyl, thienyl, pyridinyl, pyrazinyl, pyridazinyl, imidazolyl, tetrazolyl, tetrahydrofuranyl, oxazolyl, thiazolyl, thiadiazolyl, piperidinyl, morpholinyl, and piperazinyl.

In the definition of X, the term "alkenylene" includes both cis and trans structures. Suitable examples of alkenylene groups include —CH=CH—.

The compounds of formulae (X), (Xa) and (Xb) include an asymmetric centre, namely the carbon atom of the

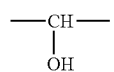

group. The present invention includes both (S) and (R) enantiomers either in substantially pure form or admixed in any proportions.

Similarly, where $R^{14}$ and $R^{15}$ are different groups, the carbon atom to which they are attached is an asymmetric centre and the present invention includes both (S) and (R) enantiomers at this centre either in substantially pure form or admixed in any proportions.

Thus the compounds of formulae (X), (Xa) and (Xb) include all enantiomers and diastereoisomers as well as mixtures thereof in any proportions.

The most preferred compound of formula (X) is 3-(4-{[6-({(2R)-2-Hydroxy-2-[4-hydroxy-3-(hydroxymethyl) phenyl]ethyl}amino)-hexyl]oxy}butyl)benzenesulfonamide or a salt or solvate thereof.

Salts and solvates of compounds of formulae (X), (Xa) and (Xb) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (X), (Xa) and (Xb) and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphoriic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Compounds of formula (X), (Xa) and (Xb) may be prepared by reference to Example X recited below, by analogous processes, or by other conventional processes known per se.

Since the compounds of formula (I) are long-acting, preferably the composition comprising the compound of formula (I) and the long-acting $\beta_2$-adrenoreceptor agonists will be delivered once-per-day and the dose of each will be selected so that the composition has a therapeutic effect in the treatment of respiratory disorders effect (eg in the treatment of asthma or COPD, particularly asthma) over 24 hours or more.

Examples of anti-histamines include methapyrilene or loratadine. Examples of anti-allergics include cromoglycate (eg as sodium), ketotifen and nedocromil (as as sodium). Examples of anti-cholinergics include ipratropium (eg as bromide), tiotropium, atropine or oxitropium. Any of the aforementioned substances may be employed in the form of alternative salts or solvates thereof.

Other suitable combinations include, for example, other anti-inflammatory agents eg. NSAIDs (eg. PDE4 inhibitors, leukotriene antagonists, iNOS inhibitors, tryptase and elastase inhibitors, beta-2 integrin antagonists and adenosine 2a agonists)) or antinfective agents (eg. antibiotics, antivirals).

Of particular interest is use of the compounds of formula (I) in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 Inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4. Initial experiments were conducted to establish and validate a [$^3$H]-rolipram binding assay. Details of this work are given in the Binding Assays described in detail below.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl [4-(3-cyclopentyloxy-4-methoxyphenyl)pyrrolidine-2-ylidene]acetate; and
(S)-(−)-ethyl [4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:
Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from Astra (Hofgen, N. et al. 15th EFMC Int Symp Med Chem (September 6–10, Edinburgh) 1998, Abst P. 98); a 9-benzyladenine derivative nominated NCS-613 (INSERM); D-4418 from Chiroscience and Schering-Plough; a benzodiazepine PDE4 inhibitor identified as CI-1018 (PD-168787; Parke-Davis/Warner-Lambert); a benzodioxole derivative Kyowa Hakko disclosed in WO 9916766; V-11294A from Napp (Landells, L. J. et al. Eur Resp J [Annu Cong Eur Resp Soc (September 19–23, Geneva) 1998] 1998, 12(Suppl. 28): Abst P2393); roflumilast (CAS reference No 162401-32-3) and a pthalazinone (WO 9947505) from Byk-Gulden; or a compound identified as T-440 (Tanabe Seiyaku; Fuji, K. et al. J Pharmacol Exp Ther, 1998, 284(1): 162).

Phosphodiesterase and Rolipram Binding Assays

Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp 1798–1804, 1992).

Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM $MgCl_2$, 50 μM 5'-AMP and 1 nM of [$^3$H]-rolipram (Torphy et al., J. of Biol. Chem., Vol. 267, No. 3 pp 1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM $MgCl_2$, 1.7 mM EGTA, [$^3$H]cAMP or [$^3$H] cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry.

[³H]R-Rolipram Binding Assay

The [³H]R-rolipram binding assay was performed by modification of the method of Schneider and co-workers, see Nicholson, et al., Trends Pharmacol. Sci., Vol. 12, pp. 19–27 (1991) and McHale et al., Mol. Pharmacol., Vol. 39, 109–113 (1991). R-Rolipram binds to the catalytic site of PDE4 see Torphy et al., Mol. Pharmacol., Vol. 39, pp. 376–384 (1991). Consequently, competition for [³H]R-rolipram binding provides an independent confirmation of the PDE4 inhibitor potencies of unlabeled competitors. The assay was performed at 30° C. for 1 hr in 0.5 µl buffer containing (final concentrations): 50 mM Tris-HCl, pH 7.5, 5 mM $MgCl_2$, 0.05% bovine serum albumin, 2 nM [³H]R-rolipram (5.7×104 dpm/pmol) and various concentrations of non-radiolabeled inhibitors. The reaction was stopped by the addition of 2.5 ml of ice-cold reaction buffer (without [³H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

The invention thus provides, in a further aspect, a combination comprising a compound of formula (I) or a physiologically acceptable solvate thereof together with a PDE4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The compounds of formula (I) and solvates thereof may be prepared by the methodology described hereinafter, constituting a further aspect of this invention.

A process according to the invention for preparing a compound of formula (I) comprises alkylation of a thioacid of formula (II)

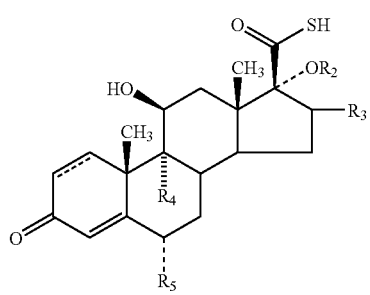

wherein $R^2$, $R^3$, $R^4$, $R^5$ and === are as defined above.

In this process the compound of formula (II) may be reacted with, for example, an appropriate alkyl or haloalkyl halide under standard conditions.

When $R_1$ represents fluoromethyl, the preferred haloalkyl halide reagent is bromofluoromethane.

Compounds of formula (II) may be prepared from the corresponding 17α-hydroxyl derivative of formula (III):

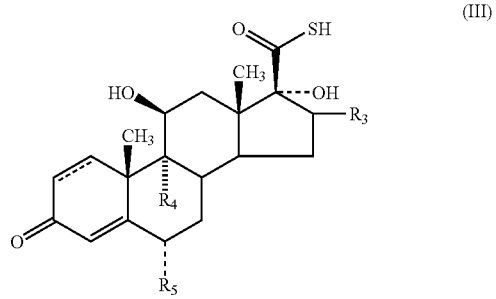

wherein $R^2$, $R^3$, $R^4$, $R^5$ and === are as defined above, using for example, the methodology described by G. H. Phillipps et al., (1994) Journal of Medicinal Chemistry, 37, 3717–3729. For example the compound of formula (III) may be reacted with a compound of formula $R_2COOH$ or an activated derivative thereof eg an activated ester, anhydride or halide (eg the acid chloride). The reaction may be performed in the presence of an organic solvent eg triethylamine, usually together with dimethylaminopyridine (DMAP).

Compounds of formula (III) may be prepared in accordance with procedures described in GB 2088877B. Compounds of formula (III) may also be prepared by a process comprising the following steps:

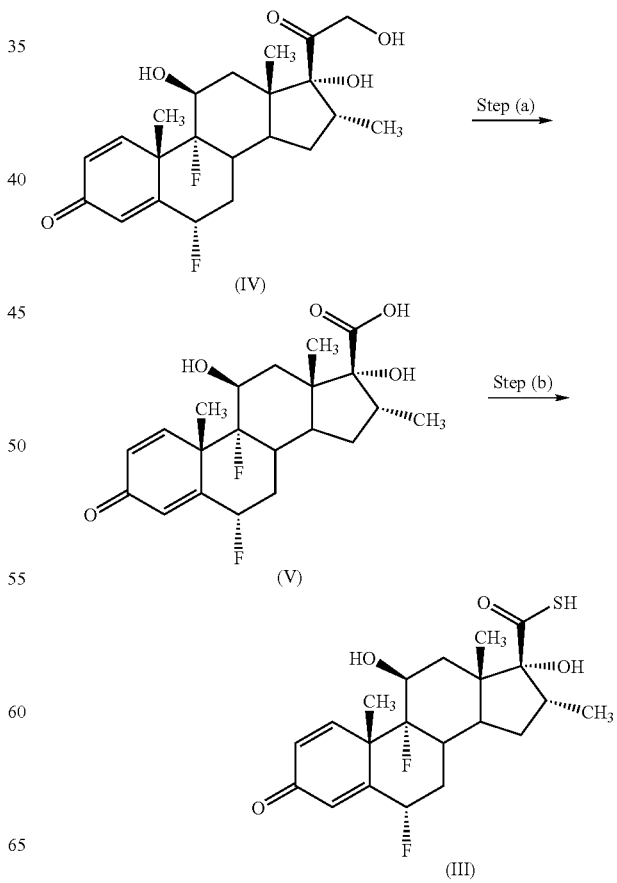

Step (a) comprises oxidation of a solution containing the compound of formula (IV). Preferably, step (a) will be performed in the presence of a solvent comprising methanol, water, tetrahydrofuran, dioxan or diethylene glygol dimethylether. For example, so as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1–9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg. one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (V) may be isolated by recrystallisation from the reaction mixture by addition of an anti-solvent. A suitable anti-solvent for compound of formula (V) is water. Surprisingly we have discovered that it is highly desirable to control the conditions under which the compound of formula (V) is precipitated by addition of anti-solvent eg water. When the recrystallisation is performed using chilled water (eg water/ice mixture at a temperature of 0–50° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no of solvated solvent within the crystal lattice.

Step (b) will typically comprise the addition of a reagent suitable for converting a carboxylic acid to a carbothioic acid eg. using hydrogen sulphide gas together with a suitable coupling agent eg. carbonyldiimidazole (CDI) in the presence of a suitable solvent eg. dimethylformamide.

Solvates of compounds of formula (I) which are not physiologically acceptable may be useful as intermediates in the preparation of compounds of formula (I) or physiologically acceptable solvates thereof.

The advantages of compounds of formula (I) and/or solvates thereof may include the fact that the substances appear to demonstrate excellent anti-inflammatory properties, with predictable pharmacokinetic and pharmacodynamic behaviour, with an attractive side-effect profile (demonstrated for example, by increased selectivity for the glucocorticoid receptor over the progesterone receptor and/or increased selectivity for glucocorticoid receptor mediated transrepression over transactivation) and are compatible with a convenient regime of treatment in human patients. Further advantages may include the fact that the substances have desirable physical and chemical properties which allow for ready manufacture and storage.

The following non-limiting Examples illustrate the invention:

EXAMPLES

General

LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a Fisons VG Plafform spectrometer using electrospray positive and negative mode (ES+ve and ES−ve).

Intermediates

Intermediate 1: 17α-(Cyclobutylcarbonyl)oxy-6α,9α-difluoro-11β-hydroxy-16α-methyl-3-oxo-androsta-1,4-diene-17β-carbothioic acid A solution of 6α,9α-difluoro-11β,17α-dihydroxy-16α-methyl-3-oxo-androsta-1,4-diene-17β-carbothioic acid (prepared in accordance with the procedure described in GB 2088877B) (1 g, 2.42 mmol) in anhydrous dichloromethane (20 ml) and triethylamine (0.88 ml, 6.32 mmol) was treated at <50° C. under nitrogen with a solution of cyclobutanecarbonyl chloride (0.72 ml, 6.31 mmol) in anhydrous dichloromethane. (5 ml) over approximately 2 min. The solution was stirred at <5° C. for 45 min and then diluted with dichloromethane (20 ml) and washed successively with 5% sodium hydrogen carbonate solution (20 m), 1 M hydrochloric acid (20 ml) and water (20 ml). The organic solution was dried ($Na_2SO_4$) and evaporated to give an off-white foam (1.47 g) which was dissolved in acetone (30 ml) and treated with 1-methylpiperazine (1 ml, 9 mmol). After 2.5 h the solution was slowly added to a stirred mixture of 2M hydrochloric acid (55 ml) and ice (55 ml) and the precipitate was collected and dried in vacuo to give the title compound as a white solid (1.12 g, 93.5%): LCMS retention time 3.79 min, m/z 495 MH$^+$ Intermediate 2: 17α-(Cyclopentylcarbonyl)oxy-6α,9α-difluoro-11β-hydroxy-16α-methyl-3-oxo-androsta-1,4-diene-17β-carbothioic acid.

Prepared using methods similar to that described for Intermediate 1. LCMS retention time 4.00 min, m/z 509 MH$^+$ Intermediate 3: 17α-(Cyclohexylcarbonyl)oxy-6α,9α-difluoro-11β-hydroxy-16α-methyl-3-oxo-androsta-1,4-diene-17β-carbothioic acid Prepared using methods similar to that described for Intermediate 1. LCMS retention time 4.17 min, m/z 523 MH$^+$ Intermediate 4: 17α-(Cyclopropylcarbonyl)oxy-6α,9α-difluoro-11β-hydroxy-16α-methyl-3-oxo-androsta-1,4-diene-17β-carbothioic acid Prepared using methods similar to that described for Intermediate 1. LCMS retention time 3.65 min, m/z 481 MH$^+$ Intermediate 5: 6α,9α-Difluoro-11β-hydroxy-16α-methyl-17α-(1-methycyclopropylcarbonyl)oxy-3-oxo-androsta-1,4-diene-17β-carbothioic acid Prepared using methods similar to that described for Intermediate 1. LCMS retention time 3.75 min, m/z 495 MH$^+$ Intermediate 6: 6α,9α-Difluoro-11β-hydroxy-16α-methyl-3-oxo-17α-(2,2,3,3-tetramethycyclopropylcarbonyl)oxy-androsta-1,4-diene-17β-carbothioic acid Prepared using methods similar to that described for Intermediate 1. LCMS retention time 4.12 min, m/z 537 MH$^+$ Intermediate 7: 17α-(2,2-Dichloro-1-methycyclopropylcarbonyl)oxy-6α,9α-difluoro-11β-hydroxy-16α-methyl-3-oxo-androsta-1,4-diene-17β-carbothioic acid Prepared using methods similar to that described for Intermediate 1. LCMS retention time 4.20 min, m/z 563,565 MH$^+$ Intermediate 8: 17α(2,2-Dichlorocylopropylcarbonyl)oxy-6α,9α-difluoro-11β-hydroxy-16α-methyl-3-oxo-androsta-1,4-diene-17βcarbothioic acid Prepared using methods similar to that described for Intermediate 1. LCMS retention time 4.14 min, m/z 549,551 MH$^+$ Intermediate 9: 6α,9α-Difluoro-11β-hydroxy-16α-methyl-17α-(3-methylenecyclobutylcarbonyl)oxy-3-oxo-androsta-1,4-diene-17β-carbothioic acid Prepared using methods similar to that described for Intermediate 1. LCMS retention time 4.10 min, m/z 507 MH$^+$ Intermediate 10: 6α,9α-Difluoro-11β-hydroxy-16α-methyl-17α-(2-methylcyclopropylcarbonyl)oxy-3-oxo-androsta-1,4-diene-17β-carbothioic acid Prepared using methods similar to that described for Intermediate 1. LCMS retention time 3.90 min, m/z 495 MH$^+$ Intermediate 11: 6α,9α-Difluoro-11β-hydroxy-16α-methyl-17α-(1-methylcyclobutylcarbonyl)oxy-3-oxo-androsta-1,4-diene-17β-carbothioic acid Prepared using methods similar to that described for Intermediate 1. LCMS retention time 4.13 min, m/z 509 MH$^+$ Intermediate 12: 6α,9α-Difluoro-17α-(3,3-dimethylcyclobutylcarbonyl)oxy-11β-hydroxy-16α-methyl-3-oxo-androsta-1,4-diene-17β-carbothioic acid Prepared using methods similar to that described for Intermediate 1. LCMS retention time 4.09 min, m/z 523 MH$^+$ Intermediate 13: 6α,9α-Difluoro-17α-(3,3-difluorocyclobutylcarbonyl)oxy-11β-hydroxy-16α-methyl-3-oxo-androsta-1,4-diene-17β-carbothioic acid Prepared using methods similar to that described for Intermediate 1. LCMS retention time 3.78 min, m/z 531 MH$^+$ Intermediate 14: 6α,9α-Difluoro-11β-hydroxy-16α-methyl-17α-(1-methylcyclopentylcarbonyl)oxy-3-oxo-androsta-1,4-diene-17β-carbothioic acid Prepared using methods similar to that described for Intermediate 1. LCMS retention time 4.05 min, m/z 523 MH+

Intermediate 15: 6α,9α-Difluoro-11β-hydroxy-16α-methyl-3-oxo-17α-(3-oxocyclobutylcarbonyl)oxy-androsta-1,4-diene-17β-carbothioic acid Prepared using methods similar to that described for Intermediate 1. LCMS retention time 3.41 min, m/z 509 MH$^+$

EXAMPLES

Example 1

17α-(Cyclobutylcarbonyl)oxy-6α,9α-difluoro-11β-hydroxy-16α-methyl-3-oxo-androsta-1,4-diene-17β-carbothioic acid S-fluoromethyl ester Sodium hydrogen carbonate (112 mg, 1.33 mmol) was added to a solution of Intermediate 1 (600 mg, 1.21 mmol) in anhydrous N,N-dimethylformamide (6 ml) and the mixture cooled to −20° C. under nitrogen. Bromofluoromethane (0.15 ml, 2.7 mmol) was added and the mixture was stirred at −20° C. for 2 h. Diethylamine (0.6 ml, 5.8 mmol) was added and the mixture stirred at −20° C. for 15 min and then added to vigorously stirred 2M hydrochloric acid (25 ml). Water (75 ml) was added and after stirring for a further 30 min the white precipitate was collected and dried in vacuo (606 mg). This material was purified was column chromatography on silica gel to give the title compound as a white solid (520 mg, 81%): LCMS retention time 3.67 min, m/z 527 MH$^+$.

Example 2

17α-(Cyclopentylcarbonyl)oxy-6α,9α-difluoro-11β-hydroxy-16α-methyl-3-oxo-androsta-1,4-diene-17β-carbothioic acid S-fluoromethyl ester Prepared from Intermediate 2 using methods similar to that described for Example 1 LCMS retention time 3.92 min, m/z 541 MH$^+$ Example 3

17α-(Cyclohexylcarbonyl)oxy-6α,9α-difluoro-11β-hydroxy-16α-methyl-3-oxo-androsta-1,4-diene-17β-carbothioic acid S-fluoromethyl ester Prepared from Intermediate 3 using methods similar to that described for Example 1 LCMS retention time 4.02 min, m/z 555 MH$^+$ Example 4

17α-(Cyclopropylcarbonyl)oxy-6α,9α-difluoro-11β-hydroxy-16α-methyl-3-oxo-androsta-1,4-diene-17β-carbothioic acid S-fluoromethyl ester Prepared from Intermediate 4 using methods similar to that described for Example 1 LCMS retention time 3.54 min, m/z 513 MH$^+$

Example 5

6α,9α-Difluoro-11β-hydroxy-16α-methyl-17α-(1-methycyclopropylcarbonyl)oxy-3-oxo-androsta-1,4-diene-17β-carbothioic acid S-fluoromethyl ester Prepared from Intermediate 5 using methods similar to that described for Example 1 LCMS retention time 3.66 min, m/z 527 MH+

Example 6

6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-fluoromethyl ester Prepared from Intermediate 6 using methods similar to that described for Example 1 LCMS retention time 4.02 min, m/z 569 MH$^+$

Example 7

17α-(2,2-Dichloro-1-methycyclopropylcarbonyl)oxy-6α,9α-difluoro-11β-hydroxy-16α-methyl-3-oxo-androsta-1,4-diene-17β-carbothioic acid S-fluoromethyl ester Prepared from Intermediate 7 using methods similar to that described for Example 1 LCMS retention time 3.79 min, m/z 595, 597, 599 MH$^+$

Example 8

17α-(2,2-Dichlorocylopropylcarbonyl)oxy-6α,9α-difluoro-11β-hydroxy-16α-methyl-3-oxo-androsta-1,4-diene-17β-carbothioic acid S-fluoromethyl ester Prepared from Intermediate 8 using methods similar to that described for Example 1 LCMS retention time 3.68 min, m/z 581, 583 MH$^+$

Example 9

6α, 9α-Difluoro-11β-hydroxy-16α-methyl-17α-(3-methylenecyclobutylcarbonyl)oxy-3-oxo-androsta-1,4-diene-17β-carbothioic acid S-fluoromethyl ester Prepared from Intermediate 9 using methods similar to that described for Example 1 LCMS retention time 3.68 min, m/z 539 MH$^+$

Example 10

6α,9α-Difluoro-11β-hydroxy-16α-methyl-17α-(2-methylcyclopropylcarbonyl)oxy-3-oxo-androsta-1,4-diene-17β-carbothioic acid S-fluoromethyl ester Prepared from Intermediate 10 using methods similar to that described for Example 1. LCMS retention time 3.57 min, m/z 527 MH$^+$

Example 11

6α,9α-Difluoro-11β-hydroxy-16α-methyl-17α-(1-methylcyclobutylcarbonyloxy-3-oxo-androsta-1,4-diene-17β-carbothioic acid S-fluoromethyl ester Prepared from Intermediate 11 using methods similar to that described for Example 1. LCMS retention time 3.73 min, m/z 541 MH$^+$

Example 12

6α,9α-Difluoro-17α-(3,3-dimethylcyclobutylcarbonyl)oxy-11β-hydroxy-16α-methyl-3-oxo-androsta-1,4-diene-17β-carbothioic acid S-fluoromethyl ester Water (1.8 ml), benzyltributylammonium chloride (35 mg) and diisopropylethylamine (0.21 ml) were added to a stirred and cooled (0° C.) solution of Intermediate 12 (585 mg, 1.12 mmol) in ethyl acetate (15 ml). A solution of bromofluoromethane (0.075 ml) in ethyl acetate (0.75 ml) was added and the mixture stirred at room temperature for 18 h. A solution of 2% diethylamine in 4:1 acetonitrile:water (1 ml) was added and the mixture stirred for 10 min. The organic phase was separated, washed successively with 0.5M hydrochloric acid, water and 1% sodium bicarbonte solution and dried and evaporated. The residue (570 mg) was purified by preparative HPLC to give the title compound as a cream solid (490 mg, 79%): LCMS retention time 3.75 min, m/z 555 MH$^+$

Example 13

6α,9α-Difluoro-17α-(3,3-difluorocyclobutylcarbonyl)oxy-11β-hydroxy-16α-methyl-3-oxo-androsta-1,4-diene-17β-carbothioic acid S-fluoromethyl ester Prepared from Intermediate 13 using methods similar to that described for Example 12. LCMS retention time 3.47 min, m/z 563 MH$^+$

Example 14

6α,9α-Difluoro-11β-hydroxy-16α-methyl-17α-(1-methylcyclopentylcarbonyl)oxy-3-oxo-androsta-1,4-diene-17α-carbothioic acid S-fluoromethyl ester Prepared from Intermediate 14 using methods similar to that described for Example 12. LCMS retention time 3.71 min, m/z 555 MH$^+$

Example 15

6α,9α-Difluoro-11β-hydroxy-16α-methyl-3-oxo-17α-(3-oxocyclobutylcarbonyl)oxy-androsta-1,4-diene-17β-carbothioic acid S-fluoromethyl ester Prepared from Intermediate 15 using methods similar to that described for Example 12. LCMS retention time 3.24 min, m/z 541 MH$^+$ Preparation of Long Acting β$_2$-Adrenoreceptor Agonist

Example X 3-(4-{[6-({(2R)-2-Hydroxy-2-[4-hydroxy-3-(hydroxymethyl)phenyl]ethyl}amino)-hexyl]oxy}butyl)benzenesulfonamide acetate i) Di(tert-butyl) 2-(2,2-dimethyl-4H-1,3-benzodioxin-6-yl)-2-oxoethylimidodicarbonate Cesium carbonate (70.4 g) was added to a stirred suspension of 2-bromo-1-(2,2-dimethyl-4H-1,3-benzodioxin-6-yl) ethanone, (Glaxo, DE 3513885, 1985) (61.8 g) and di-t-butyl iminodicarboxylate (47.15 g) in acetonitrile (600 ml) under nitrogen. After vigorous stirring at 21° C. for 24 h the mixture was diluted with water (ca800 ml) and the product was extracted with diethyl ether (1 liter, then 200 ml). The combined organic layers were washed with brine, dried (MgSO$_4$) and concentrated to ca400 ml. The white crystals were collected by filtration, washed with diethyl ether and dried to give the title compound (24.4 g) δ (CDCl$_3$) 7.78 (1H, dd, J 8, 2 Hz), 7.65 (1H, brs), 6.87 (1H, d, J 8 Hz), 4.97(2H, s), 4.88(2H, s), 1.56(6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

ii) tert-Butyl 2-(2,2-dimethyl-4H-1,3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 liters) at 21° C. and the reaction was stirred for 1.5 h. Aqueous NaOH solution (1.75 liters) was added and after 10 min the phases were separated. The organic layer was washed with water, dried (MgSO$_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

iii) tert-Butyl(2R)-2-(2,2-dimethyl-4H-1,3-benzodioxin-6-yl)-2-hydroxyethylcarbamate A 2M solution of borane-dimethyl sulphide in THF (28 ml) was added slowly to a 1 M solution of (R)-tetrahydro-1-methyl-3,3-diphenyl-1H,3H-pyrrolo[1,2-c][1,3,2]oxazaborole in toluene (56 ml) at 0° C. under nitrogen. A solution of tert-butyl 2-(2,2-dimethyl-4H-1,3-benzodioxin-6-yl)-2-oxoethylcarbamate, (108.2 g) in THF (1.3 liters) was added slowly keeping the temperature below 5° C. followed by 2M solution of borane-dimethyl sulphide in THF (252 ml) over 50 min. After 1 h, 2M HCl (170 ml) was added with cooling and the mixture was partitioned between ethyl acetate and water. The organic layer was washed with saturated NaHCO$_3$ solution and brine and dried (MgSO$_4$). The solution was concentrated and the product purified by chromatography on flash silica gel (800 g), eluting successively with hexane:ethyl acetate (4:1 then 3:1) to give the title compound (93.3 g), LCMS RT=3.31 min.

iv) (5R)-5-(2,2-Dimethyl-4H-1,3-benzodioxin-6-yl)-1,3-oxazolidin-2-one tert-Butyl(2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° C. under nitrogen. The mixture was stirred at 21° C. for 2 h. The mixture was recooled to 0° C. and 2M HCl (134 ml) was added. The mixture was diluted with water and the product was extracted with ethyl acetate twice. The solution was washed with brine twice, dried (MgSO$_4$) and evaporated to give the title compound (63.55 g) LCMS RT=2.66 min.

v) 6-Bromohexyl but-3-ynyl ether

3-Butyn-1-ol (42.4 ml) was stirred vigorously with 1,6-dibromohexane (260 ml) and tetrabutylammonium bisulphate (2.4 g) in 50% aqueous sodium hydroxide solution (200 ml) under nitrogen for 3 days. Water (ca 700 ml) was added and the organic layer was separated. The aqueous layer was extracted twice with dichloromethane (2×100 ml) and the combined organic layers were washed with water, dried (MgSO$_4$) and concentrated. The residue in petroleum ether (bp 40–60°) was loaded onto a column of silica gel (1.5 kg) and the column was eluted with petroleum ether (bp 40–60° C.), then 10% diethyl ether in petroleum ether (bp 40–60° C.) to give the title compound (103.3 g), δ (CDCl$_3$) 3.56(2H, t, J 7 Hz), 3.47(2H, t, J 7 Hz), 3.42(2H, t. J 7 Hz), 2.45(2H, m), 1.99(1H, t, J 2 Hz),1.87(2H, m), 1.60(2H, m) and 1.50 to 1.33 (4H, m).

vi) (5R)-3-[6-(But-3-ynyloxy)hexyl]-5-(2,2-dimethyl-4H-1,3-benzodioxin-6-yl)-1,3-oxazolidin-2-one (5R)-5-(2,2-dimethyl-4H-1,3-benzodioxin-6-yl)-1,3-oxazolidin-2-one (10 g) in DMF (100 ml) was added dropwise to a stirred suspension of sodium hydride (60% oil dispersion, 2.33 g) in DMF (50 ml) with stirring under nitrogen and maintaining the internal temperature at 0° C. Stirring was continued at 0–5° C. for 1 h. The mixture was recooled to 0° C. and a solution of 6-bromohexyl but-3-ynyl ether (14.7 g) in DMF (50 ml) was added over 1 min. The mixture was then stirred at 20–30° C. for 2 h. 2M HCl (9 ml) was added and the mixture was partitioned between water and diethyl ether. The aqueous layer was extracted with more diethyl ether and the combined organic layers were washed twice with brine. After drying (MgSO$_4$) the solution was concentrated and loaded onto a column of silica gel (600 g) set up in diethyl ether:petroleum ether (bp 40–60° C.) (1:2). The column was eluted successively with this mixture, then (1:1) and then diethyl ether to give the title compound (13.88 g) LCMS RT=3.45 min.

vii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide (5R)-3-[6-(But-3-ynyloxy)hexyl]5-(2,2-dimethyl-4H-1,3-benzodioxin-6-yl)-1,3-oxazolidin-2-one (1.79 g) was stirred with 3-iodobenzene sulphonamide (1.4 g) in acetonitrile:triethylamine (1:1, 42 ml) under nitrogen for 10 min. Cuprous iodide (0.083 g) and dichlorobis(triphenylphosphine)palladium (0.192 g) were added and the mixture was stirred for 17 h under nitrogen at 21° C. The mixture was evaporated to dryness and the residue was chromatographed on silica gel (250 g) in 30% ethyl acetate: petroleum ether (bp 40–60°), then 50%, then 75% and finally ethyl acetate to give the title compound (2.35 g), LCMS RT=3.44 min.

viii) 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide 3-[4-({6-[(5R)-5-(2,2-dimethyl-4H-1,3-benzodioxin-6-yl)-2-oxo-1,3-oxazolidin-3-yl]hexyl}oxy)but-1-ynyl]benzenesulfonamide (2.35 g) was stirred with platinum oxide (0.3 g) in THF (30 ml) under hydrogen for 2 h. The catalyst was removed by filtration using a filter aid and the filter cake was leached with ethyl acetate. The combined filtrates were passed through silica gel (200 g) in ethyl acetate and the eluate was evaporated to give the title compound (2.32 g), LCMS RT=3.49 min.

ix) 3-{4-[(6-{[(2R)-2-(2,2-Dimethyl-4H-1,3-benzodioxin-6-yl)-2-hydroxyethyl]amino}hexyl)oxy]butyl}benzenesulfonamide 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide (0.43 g) was stirred in THF (10 ml) while purging with a vigorous stream of nitrogen for 5 min. Potassium trimethylsilanoate (0.43 g) was added and the mixture was stirred at 70° C. under nitrogen for 2.5 h. The mixture was partitioned between dichloromethane and pH 6.4 phosphate buffer and the aqueous layer was extracted with more dichloromethane. The combined organic layers were washed with water, dried (MgSO$_4$) and concentrated. The residue was purified on silica gel (60 g), eluting successively with ethyl acetate:petroleum ether (bp 40–60° C.) (1:1), ethyl acetate, 10% then 20% methanol in ethyl acetate to give the title compound (0.286 g), LCMS RT=2.56 min.

x) 3-(4-{[6-({(2R)-2-Hydroxy-2-[4-hydroxy-3-(hydroxymethyl)phenyl]ethyl}amino)-hexyl]oxy}butyl)benzenesulfonamide acetate 3-{4-[(6-{[(2R)-2-(2,2-dimethyl-4H-1,3-benzodioxin-6-yl)-2-hydroxyethyl]amino}hexyl)oxy]butyl}benzenesulfonamide (0.283 g) was stirred with acetic acid (8 ml) and water (4 ml) at 70° for 35 min before evaporating to dryness. The residue was re-evaporated twice with toluene to give the title compound (0.318 g) LCMS RT=2.34 min, ES+ve 495 (MH)$^+$.

Pharmacological Activity

Pharmacological activity was assessed in a functional in vitro assay of glucocorticoid agonist activity which is generally predictive of anti-inflammatory or anti-allergic activity in vivo.

The functional assay was based on that described by K. P. Ray et al., Biochem J. (1997), 328, 707–715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which EC$_{50}$ values were estimated. In this test the compounds of Examples 1 to 15 showed an EC$_{50}$ value of <2 nM.

Screen for Progesterone Receptor Activity

The human breast cancer cell line T47D has been reported to upregulate an endogenous alkaline phosphatase in response to progestins (Di Lorenzo et al., Cancer Research (1991) 51, 4470–4475. T47D cells were seeded into 96 well plates at a density of 1×10$^5$ cells per well and grown overnight at 37° C. Steroids were dissolved in DMSO, added to the cells (final DMSO concentration 0.7%), and incubated for 24 hours at 37° C. The cells were then washed with PBS and lysed with RIPA buffer (1% IGEPAL, 0.5% Na deoxycholate, 0.1% SDS in phosphate buffered saline). Alkaline phosphatase activity was measured spectrophotometrically (405 nm) using p-nitrophenylphosphate (1.5 mg/ml) as a substrate dissolved in 1M diethanolamine, 0.28M NaCl, 0.5 mM MgCl$_2$. Dose response curves were constructed from which EC$_{50}$ values were estimated.

Examples 5 and 11 were tested for progesterone activity in accordance with the above screen and the selectivity was determined by dividing the ED$_{50}$ at the progesterone receptor by the ED$_{50}$ at the glucocorticoid receptor. The selectivity of Example 5 was 353 (compare fluticasone propionate: selectivity=57) and of Example 11 was 1230 (compare fluticasone propionate: selectivity=107).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps. The patents and patent applications described in this application are herein incorporated by reference.

What is claimed is:

1. A compound of formula (I)

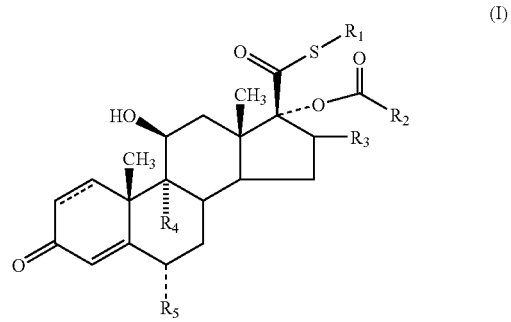

wherein
R$_1$ represents C$_{1-6}$ alkyl or C$_{1-6}$ haloalkyl;
R$_2$ represents C$_{3-8}$ cycloalkyl or C$_{3-8}$ cycloalkenyl either of which may optionally be substituted by one or more groups selected from oxo, methyl, methylene and halogen;
R$_3$ represents hydrogen, methyl (which may be in either the α or β configuration) or methylene;
R$_4$ and R$_5$ are the same or different and each represents hydrogen or halogen; and
═══ represents a single or a double bond;
or a solvate thereof.

2. A compound according to claim 1 in which R$_2$ represents C$_{3-8}$ cycloalkyl or C$_{3-8}$ cycloalkenyl either of which may optionally be substituted by one or more groups selected from methyl, methylene and halogen.

3. A compound according to claim 1 in which R$_2$ represents C$_{3-6}$ cycloalkyl optionally substituted by one or more methyl and/or chlorine groups.

4. A compound according to claim 1 in which R$_1$ represents fluoromethyl, chloromethyl, bromomethyl or 2'-fluoroethyl.

5. A compound according to claim 4 in which R$_1$ represents fluoromethyl.

6. A compound according to claim 1 in which R$_3$ is methyl.

7. A compound according to claim 1 in which R$_4$ and R$_5$ are the same or different and each represents hydrogen, fluorine or chlorine.

8. A compound according to claim 7 in which $R_4$ and $R_5$ are the same or different and each represents hydrogen or fluorine.

9. A compound according to claim 8 in which both $R_4$ and $R_5$ are fluorine.

10. A compound according to claim 1 in which ═══ represents a double bond.

11. A compound according to claim 1 which is:
17α-(Cyclobutylcarbonyl)oxy-6α,9α-difluoro-11β-hydroxy-16α-methyl-3-oxo-androsta-1,4-diene-17β-carbothioic acid S-fluoromethyl ester;
17α-(Cyclopentylcarbonyl)oxy-6α,9α-difluoro-11β-hydroxy-16α-methyl-3-oxo-androsta-1,4-diene-17β-carbothioic acid S-fluoromethyl ester;
17α-(Cyclohexylcarbonyl)oxy-6α,9α-difluoro-11β-hydroxy-16α-methyl-3-oxo-androsta-1,4-diene-17β-carbothioic acid S-fluoromethyl ester;
17α-(Cyclopropylcarbonyl)oxy-6α,9α-difluoro-11β-hydroxy-16α-methyl-3-oxo-androsta-1,4-diene-17β-carbothioic acid S-fluoromethyl ester;
or a solvate of any one thereof.

12. A compound according to claim 1 which is:
6α,9α-Difluoro-11β-hydroxy-16α-methyl-17α-(1-methycyclopropylcarbonyl)oxy-3-oxo-androsta-1,4-diene-17β-carbothioic acid S-fluoromethyl ester;
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-fluoromethyl ester;
17α-(2,2-Dichloro-1-methycyclopropylcarbonyl)oxy-6α,9α-difluoro-11β-hydroxy-16α-methyl-3-oxo-androsta-1,4-diene-17β-carbothioic acid S-fluoromethyl ester;
17α-(2,2-Dichlorocyclopropylcarbonyl)oxy-6α,9α-difluoro-11β-hydroxy-16α-methyl-3-oxo-androsta-1,4-diene-17β-carbothioic acid S-fluoromethyl ester;
6α,9α-Difluoro-11β-hydroxy-16α-methyl-17α-(3-methylenecyclobutylcarbonyl)oxy-3-oxo-androsta-1,4-diene-17β-carbothioic acid S-fluoromethyl ester;
6α,9α-Difluoro-11β-hydroxy-16α-methyl-1,7α-(2-methylcyclopropylcarbonyl)oxy-3-oxo-androsta-1,4-diene-17β-carbothioic acid S-fluoromethyl ester;
or a solvate of any one thereof.

13. A compound according to claim 1 which is:
6α,9α-Difluoro-11β-hydroxy-16α-methyl-17α-(1-methylcyclobutylcarbonyl) oxy-3-oxo-androsta-1,4-diene-17β-carbothioic acid S-fluoromethyl ester;
or a solvate thereof.

14. A compound according to claim 1 which is:
6α,9α-Difluoro-17α-(3,3-dimethylcyclobutylcarbonyl)oxy-11β-hydroxy-16α-methyl-3-oxo-androsta-1,4-diene-17β-carbothioic acid S-fluoromethyl ester;
6α,9α-Difluoro-17α-(3,3-difluorocyclobutylcarbonyl)oxy-11β-hydroxy-16α-methyl-3-oxo-androsta-1,4-diene-17β-carbothioic acid S-fluoromethyl ester;
6α,9α-Difluoro-11β-hydroxy-16α-methyl-17α-(1-methylcyclopentylcarbonyl)oxy-3-oxo-androsta-1,4-diene-17β-carbothioic acid S-fluoromethyl ester;
6α,9α-Difluoro-11β-hydroxy-16α-methyl-3-oxo-17α-(3-oxocyclobutylcarbonyl)oxy-androsta-1,4-diene-17β-carbothioic acid S-fluoromethyl ester;
or a solvate of any one thereof.

15. A compound: 6α,9α-Difluoro-11β-hydroxy-16α-methyl-17α-(1-methycyclopropylcarbonyl) oxy-3-oxo-androsta-1,4-diene-17β-carbothioic acid S-fluoromethyl ester or a physiologically acceptable solvate thereof.

16. A pharmaceutical composition comprising a compound of formula (I) as defined in claim 1 or a physiologically acceptable solvate thereof in admixture with one or more physiologically acceptable diluents or carriers.

17. A pharmaceutical aerosol formulation comprising a compound of formula (I) as defined in claim 1 or a physiologically acceptable solvate thereof, and a fluorocarbon or hydrogen-containing chlorofluoro carbon as propellant, optionally in combination with a surfactant and or a cosolvent.

18. A pharmaceutical composition according to claim 16 which further comprises another therapeutically active agent.

19. A pharmaceutical composition according to claim 18 in which said another therapeutically active agent is a $\beta_2$-adrenoreceptor agonist.

20. A pharmaceutical composition according to claim 19 in which said $\beta_2$-adrenoreceptor agonist is a compound of formula (X):

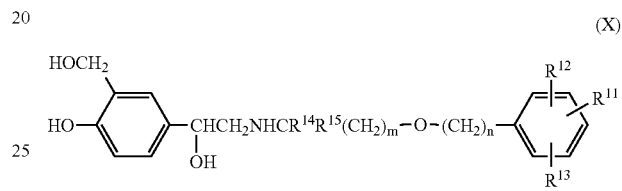

or a salt or solvate thereof, wherein:
m is an integer of from 2 to 8;
n is an integer of from 3 to 11,
with the proviso that m+n is 5 to 19,
$R^{11}$ is —$XSO_2NR^{16}R^{17}$ wherein X is —$(CH_2)_p$— or $C_{2-6}$ alkenylene;
$R^{16}$ and $R^{17}$ are independently selected from hydrogen, $C_{1-6}$alkyl, $C_{3-7}$cycloalkyl, $C(O)NR^{18}R^{19}$, phenyl, and phenyl ($C_{1-4}$alkyl)-, or $R^{16}$ and $R^{17}$, together with the nitrogen to which they are bonded, form a 5-, 6-, or 7-membered nitrogen containing ring, and $R^{16}$ and $R^{17}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{18}$, —$SO_2NR^{18}R^{19}$, —$CONR^{18}R^{19}$, —$NR^{18}C(O)R^{19}$, or a 5-, 6- or 7-membered heterocylic ring;
$R^{18}$ and $R^{19}$ are independently selected from hydrogen, $C_{1-6}$alkyl, $C_{3-6}$cycloalkyl, phenyl, and phenyl ($C_{1-4}$alkyl)-; and
p is an integer of from 0 to 6;
$R^{12}$ and $R^{13}$ are independently selected from hydrogen, $C_{1-6}$alkyl, $C_{1-6}$alkoxy, halo, phenyl, and $C_{1-6}$haloalkyl; and
$R^{14}$ and $R^{15}$ are independently selected from hydrogen and $C_{1-4}$alkyl with the proviso that the total number of carbon atoms in $R^{14}$ and $R^{15}$ is not more than 4.

21. A pharmaceutical composition according to claim 19 in which the compound of formula (X) is 3-(4-{[6-({(2R)-2-Hydroxy-2-[4-hydroxy-3-(hydroxymethyl)phenyl] ethyl}amino)-hexyl]oxy}butyl)benzenesulfonamide or a salt or solvate thereof.

22. A pharmaceutical composition according to claim 18 in which said another therapeutically active agent is an antihistamine.

23. A pharmaceutical composition according to claim 22 in which said antihistamine is methapyrilene or loratadine.

24. A pharmaceutical composition according to claim 22 in which the compound of formula (I) is 6α,9α-difluoro- 11β-hydroxy-16α-methyl-17α-(1-methycyclopropylcarbonyl)oxy-3-oxo-androsta-1,4-diene-17β-carbothioic acid S-fluoromethyl ester.

25. A pharmaceutical composition according to claim 23 in which the compound of formula (I) is 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester.

26. A pharmaceutical composition according to claim 16 wherein the composition is a aerosol formulation administered to the nose by a pump.

27. A pharmaceutical composition according to claim 16 wherein the composition is an aqueous aerosol formulation.

28. A pharmaceutical composition according to claim 27 wherein the formulation is non-pressurised and adapted to be administered topically to the nasal cavity.

29. A pharmaceutical composition according to claim 28 further comprising a buffering agent and/or a tonicity modifying agent.

30. The pharmaceutical composition according to claim 16 wherein the pharmaceutical composition is in an aqueous formulation and is administered to the nose by nebulisation.

31. A pharmaceutical composition comprising a compound as defined in claim 15 in admixture with one or more physiologically acceptable diluents and/or carriers.

32. A pharmaceutical composition according to claim 31 wherein the composition is an aerosol formulation.

33. A pharmaceutical composition according to claim 32 wherein the composition is an aqueous aerosol formulation.

34. A pharmaceutical composition according to claim 33 wherein the formulation is non-pressurised and adapted to be administered topically to the nasal cavity.

35. A pharmaceutical composition according to claim 33 further comprising a buffering agent and/or a tonicity modifying agent.

36. A method of treatment of at least one inflammatory and/or allergic condition comprising delivery to a patient a compound of formula (I) as defined claim 1 or a physiologically acceptable solvate thereof.

37. A method for the treatment of a human or animal subject with an anti-inflammatory and/or allergic condition, which method comprises administering to said human or animal subject an effective amount of a compound of formula (I) as defined in claim 1 or a physiologically acceptable solvate thereof.

38. A method of treatment of at least one inflammatory and/or allergic condition comprising delivery to a patient a compound of claim 15.

39. The method of treatment of claim 38 wherein the pharmaceutical composition is an aqueous formulation and is administered to the nose.

40. The method of treatment of claim 39 wherein said at least one inflammatory and/or allergic condition is rhinitis.

41. A method of making a veterinary or human medicine comprising admixing a compound of formula (I) as defined in claim 1 or a physiologically acceptable solvate thereof in a pharmaceutically acceptable dosage form.

42. A method of making a veterinary or human medicine comprising admixing a compound of claim 15 in a pharmaceutically acceptable dosage form.

43. A process for preparing a compound of formula (I) according to claim 1 which comprises alkylation of a compound of formula (II)

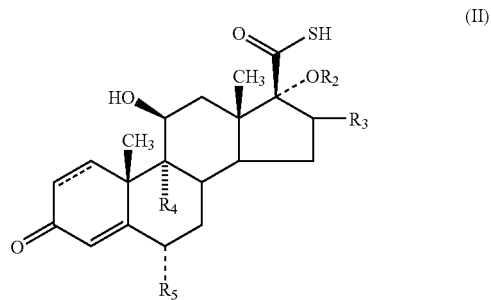

wherein $R^2$, $R^3$, $R^4$, $R^5$ and ═══ are as defined in claim 1.

44. A process according to claim 28 wherein alkylation is performed by reacting the compound of formula (II) with an appropriate alkyl or haloalkyl halide.

45. A compound of formula (II)

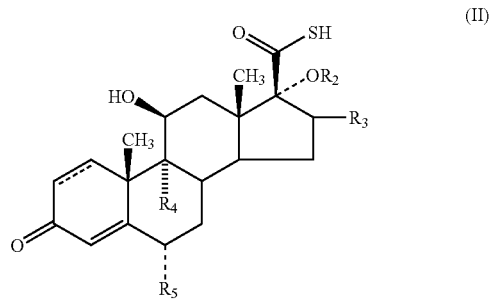

wherein $R^2$, $R^3$, $R^4$, $R^5$ and ═══ are as defined in claim 1.

* * * * *

UNITED STATES PATENT AND TRADEMARK OFFICE
CERTIFICATE OF CORRECTION

PATENT NO. : 7,291,608 B2
APPLICATION NO. : 10/478893
DATED : November 6, 2007
INVENTOR(S) : Keith Biggadike, Paul Jones and Jeremy John Payne It is certified that error appears in the above-identified patent and that said Letters Patent is hereby corrected as shown below:

In Col. 1, line 53:

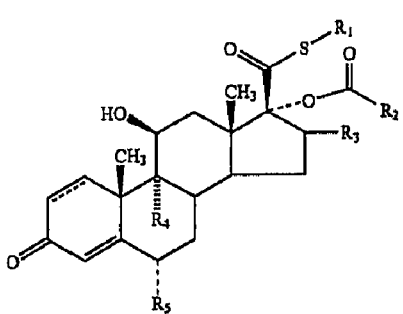   Should read:   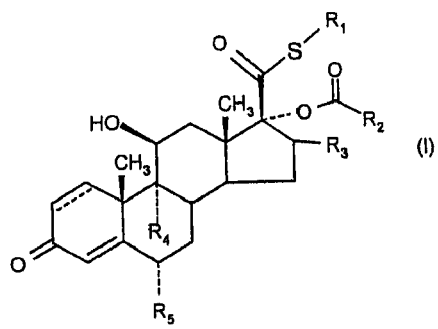

In Col. 13, line 46:

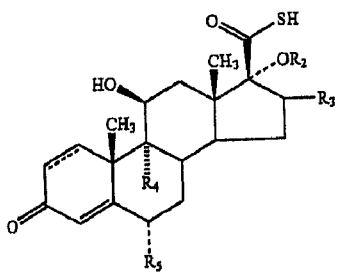   Should read:   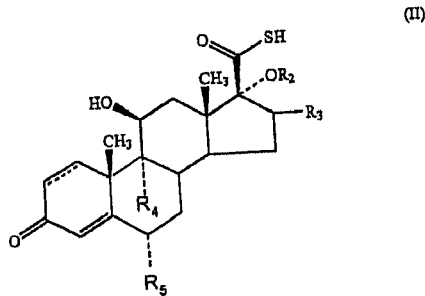

In Col. 14, line 3:

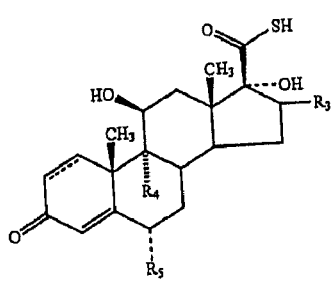   Should read:   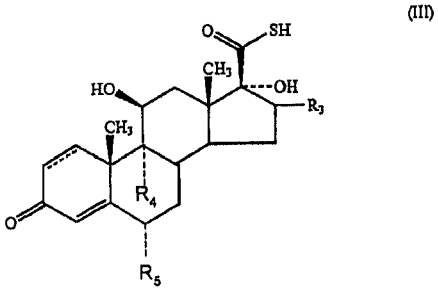

UNITED STATES PATENT AND TRADEMARK OFFICE
CERTIFICATE OF CORRECTION

PATENT NO. : 7,291,608 B2
APPLICATION NO. : 10/478893
DATED : November 6, 2007
INVENTOR(S) : Keith Biggadike, Paul Jones and Jeremy John Payne It is certified that error appears in the above-identified patent and that said Letters Patent is hereby corrected as shown below:

In Col. 24, line 24 Claim 1:

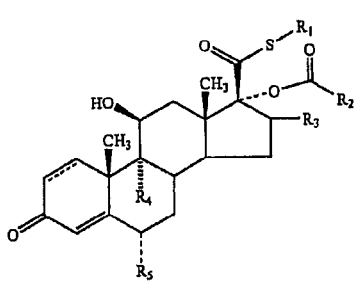  Should read: 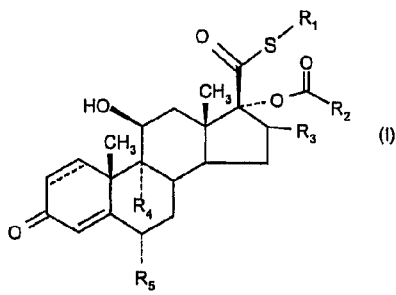

In Col. 28, line 15, Claim 43:

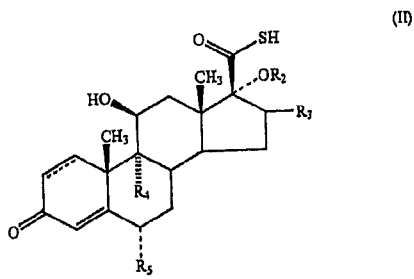  Should read: 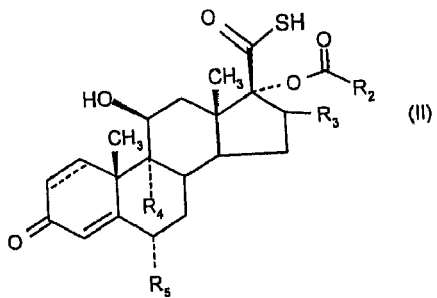

UNITED STATES PATENT AND TRADEMARK OFFICE
CERTIFICATE OF CORRECTION

PATENT NO. : 7,291,608 B2
APPLICATION NO. : 10/478893
DATED : November 6, 2007
INVENTOR(S) : Keith Biggadike, Paul Jones and Jeremy John Payne It is certified that error appears in the above-identified patent and that said Letters Patent is hereby corrected as shown below:

In Col. 28, line 35, Claim 45:

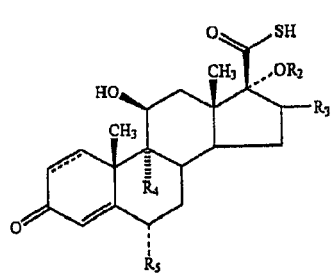 Should read: 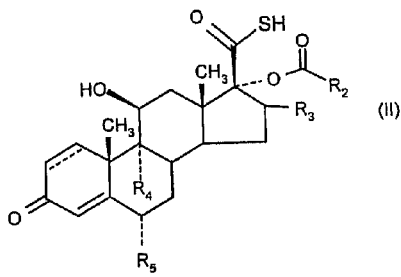

Signed and Sealed this

Second Day of December, 2008

JON W. DUDAS
*Director of the United States Patent and Trademark Office*